United States Patent [19]

Sustmann

[11] Patent Number: 4,563,398

[45] Date of Patent: Jan. 7, 1986

[54] BLANK USEFUL IN THE PRODUCTION OF A TAMPON FOR FEMININE HYGIENE

[75] Inventor: Scarlet Sustmann, Viersen, Fed. Rep. of Germany

[73] Assignee: Henkel Kommanditgesellschaft auf Aktien, Duesseldorf, Fed. Rep. of Germany

[21] Appl. No.: 536,176

[22] Filed: Sep. 27, 1983

[30] Foreign Application Priority Data

Oct. 2, 1982 [DE] Fed. Rep. of Germany ....... 3236541

[51] Int. Cl.$^4$ ............................................. A61F 13/20
[52] U.S. Cl. .................................. 428/542.8; 604/375; 604/904
[58] Field of Search ................... 28/118, 119; 604/374, 604/375, 904; 428/542.8, 297

[56] References Cited

U.S. PATENT DOCUMENTS

| | | | |
|---|---|---|---|
| 3,618,605 | 11/1971 | Glassman | 604/286 |
| 3,654,928 | 4/1972 | Duchane | 428/913 X |
| 3,746,592 | 7/1973 | Nystrand et al. | 156/202 |
| 3,868,287 | 2/1975 | Lewyckyj | 156/202 X |
| 3,968,798 | 7/1976 | Hokanson | 604/368 |
| 3,976,075 | 8/1976 | Chinai et al. | 604/376 X |
| 4,081,884 | 4/1978 | Johst et al. | 28/119 |
| 4,144,623 | 3/1979 | Steffens | 28/118 |
| 4,226,237 | 10/1980 | Levesque | 604/375 X |
| 4,289,130 | 9/1981 | Usami et al. | 428/297 X |
| 4,294,253 | 10/1981 | Friese | 428/297 X |
| 4,315,507 | 2/1982 | Whitehead et al. | 428/297 X |
| 4,359,357 | 11/1982 | Friese | 156/201 |
| 4,391,869 | 7/1983 | Cook et al. | 428/288 X |
| 4,413,995 | 11/1983 | Korpman | 428/287 X |

FOREIGN PATENT DOCUMENTS 1135004 11/1982 Canada .

*Primary Examiner*—Henry F. Epstein
*Attorney, Agent, or Firm*—Ernest G. Szoke; Nelson Littell, Jr.; Henry E. Millson, Jr.

[57] ABSTRACT

A blank useful in the production of a tampon for feminine hygiene consist of a length of cottonwool or rayon staple or combination of it strip wrapped in a moisture-pervious, fluff-free covering material. According to the invention, a covering material consisting at least partly of thermoplastic fibers is used and is sealed at its exposed edges to enclose the length of cottonwool strip in a fluffproof form.

6 Claims, 6 Drawing Figures

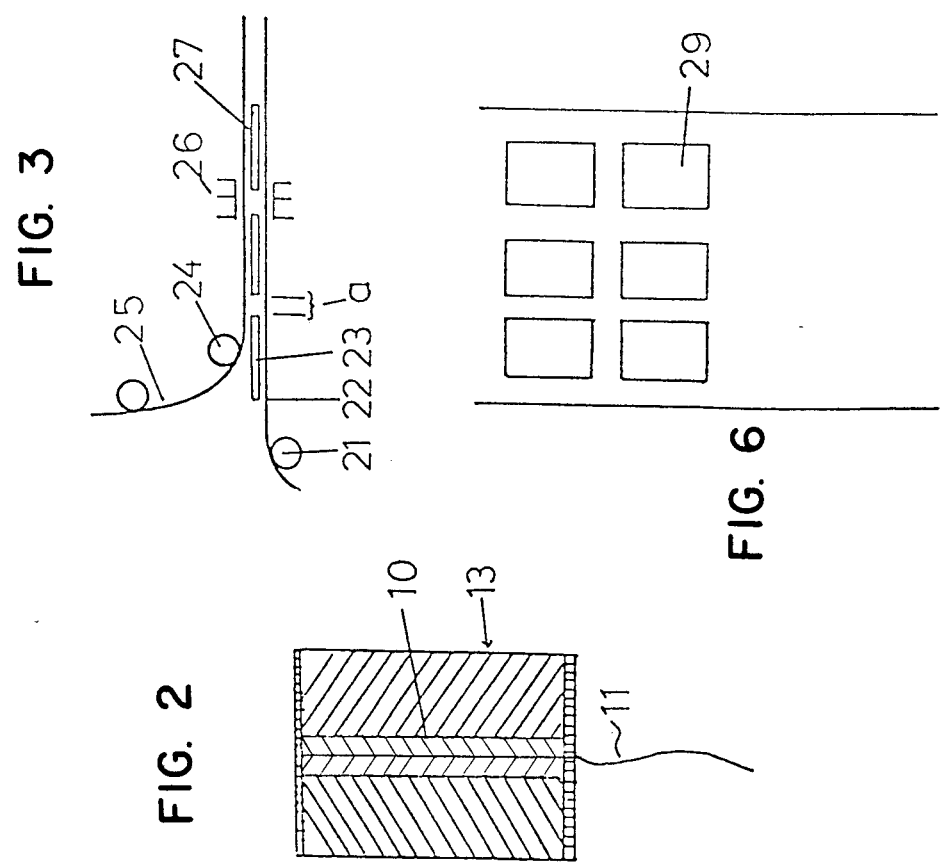

BLANK USEFUL IN THE PRODUCTION OF A TAMPON FOR FEMININE HYGIENE

BACKGROUND OF THE INVENTION

This invention relates to a blank useful in the production of a tampon for feminine hygiene consisting of a length of a strip of cottonwool or rayon staple or combination thereof sealed in a moisture-pervious fluff-free covering material. The blank is then supplied with a recovery thread and compressed radially and/or axially in relation to the recovery thread. The invention also relates to a process for producing the blank useful in the production of a tampon.

With conventional tampons, fibers or pieces of cottonwool can remain behind in the vagina. Accordingly, attempts have been made to cover the length of fibrous cottonwool strip with moisture-pervious fluff-free material in the manufacture of tampons. The covering in question may consist, for example, of rayon, synthetic fibers or of a mixture of these materials, preferably in a nonwoven form. For example, tampons, are produced by a process in which the rectangular length of cottonwool strip is wrapped in a nonwoven and the associated recovery thread or recovery string is sewn on longitudinally of the strip. In that case, compression may be carried out radially and/or axially in relation to the longitudinal axis of the strip.

Where compression is carried out radially, W-shaped folding, i.e. four-layer, folding is preferred. However, this process does not enable the tampon to be covered at its cut edges, i.e. at the head of the tampon and at its end, so that fibers are able to break loose there, i.e. to break out from the cottonwool strip.

In another process used for producing tampons, the strip of cottonwool is wrapped in a nonwoven and then cut into rectangular sections. The length of the section to be compressed is determined by the width of the cottonwool strip. Accordingly, the recovery thread is fastened perpendicularly of rather than parallel to the overlap line of the covering material. In this process, too, W-shaped folding of the covered section of cottonwool strip is preferred, although the fold lines run paralled to the exposed cut edges. In this way, the exposed cut edge are displaced from the head and the head and the end of the tampon onto its substantially cylindrical peripheral surface, although they are still exposed. Accordingly, fibers can become detached from the cut edges on removal of the tampon, particularly after it has expanded on taking up fluid.

OBJECT OF THE INVENTION

An object of the present invention is to obtain a blank for the production of a tampon for feminine hygiene, which blank is completely enclosed in fluff-free or fuzz-free material in such a way that, after attaching a recovery thread thereto and cylindrically compressing the same into a tampon, no fibers are able to break loose.

Another object of the present invention is the development of a blank useful in the production of a tampon for feminine hygiene comprising a desired length of a cottonwool or rayon staple or combination thereof strip in a moisture-pervious fluff-free or fuzz-free covering material consisting at least partially of thermoplastic fibers where any edges of said length of cottonwool strip remaining open or exposed after combination with said length of cottonwool strip are sealed to enclose the length of cottonwool or rayon staple or combination thereof strip in fluff-proof or fuzz-proof form.

A yet further object of the present invention is the development of a process for the production of a blank useful in the production of a tampon for feminine hygiene comprising the steps of (1) delivering individual lengths of strips of cottonwool or rayon staple or combination thereof onto a strip of covering material, at preselected intervals, (2) covering said individual lengths of cottonwool strip or rayon staple or combination of it with said covering material, said covering material in steps (1) and (2) being a moisture-pervious fluff-free or fuzz-free covering material consisting at least partially of thermoplastic fibers, (3) sealing in fluffproof form the projecting surfaces of said covering material around the periphery of said individual lengths of cottonwool strip or rayon staple or combination of it, (4) separating fluff-proof or fuzz-proof covered and sealed individual lengths of cottonwool strip or rayon staple or combination of it, either before during or after said sealing step, and (5) recovering a blank useful in the production of a tampon for feminine hygiene.

These and other objects of the invention will become more apparent as the description thereof proceeds.

THE DRAWINGS

FIG. 2 shows a length of cottonwool strip or rayon staple or combination of it provided with a recovery thread.

FIG. 3 shows the introduction of individual lengths of cottonwool strip or rayon staple or combination of it between two layers of covering material in a sandwich process.

FIG. 4 is a plan view of a length of cottonwool strip or rayon staple or combination of it with fluffproof covering material stamped and sealed around it.

FIG. 5 shows a roller for producing several covered sections adjacent one another.

FIG. 6 is a plan view of a web comprising several longitudinally and transversely divided lengths of cottonwool strip or rayon staple or combination of it sealed in a fluffproof or fuzz-proof covering material.

DESCRIPTION OF THE INVENTION

Figure 1:
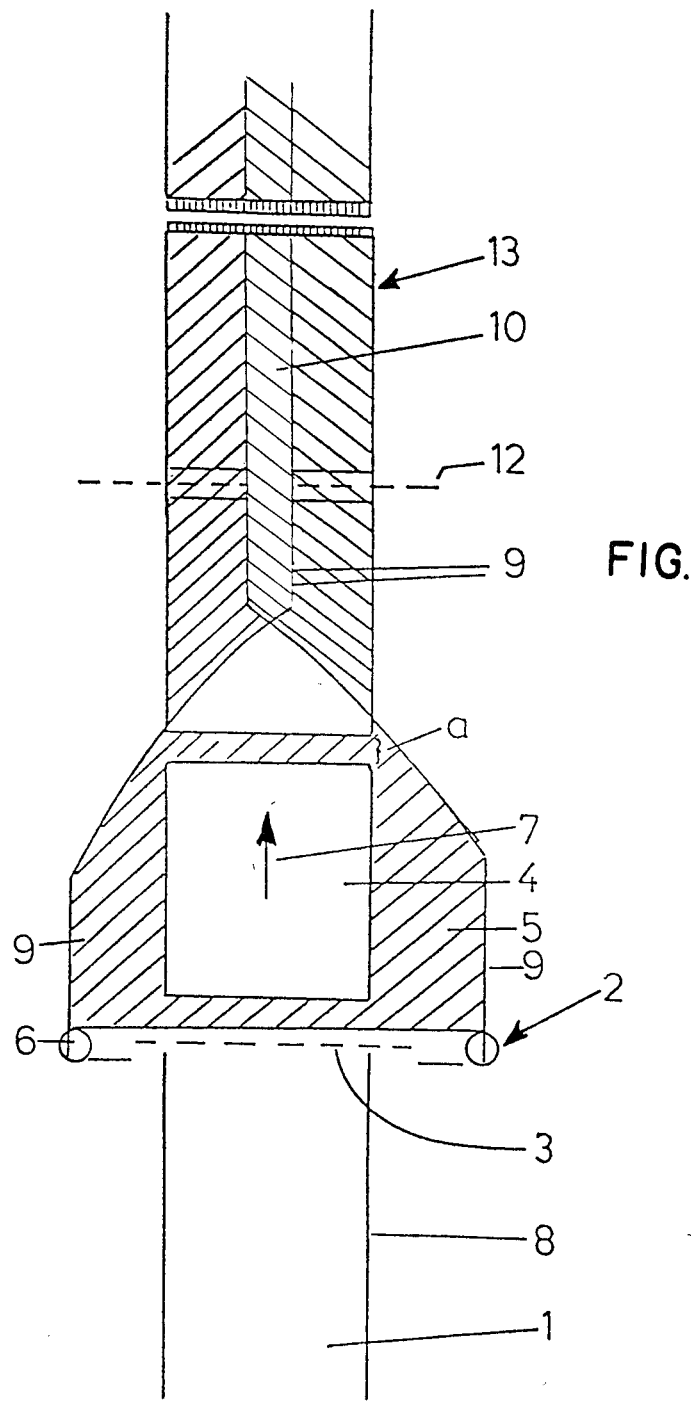
FIG. 1 shows the successive phases of a folding, stamping and sealing process for producing lengths of cottonwool strip or rayon staple or combination of it covered in fluffproof or fuzz-proof form.

The present invention relates to a blank useful in the production of a tampon for feminine hygiene which is a length of a strip of cottonwool or rayon staple or combination thereof completely sealed in a moisture-pervious fluffproof or fuzz-proof covering material. More particularly, the present invention relates to a blank useful in the production of a tampon for feminine hygiene comprising a desired length of a cottonwool strip or rayon staple or combination of it in a moisture-pervious fluff-free or fuzz-free covering material consisting at least partially of thermoplastic fibers where any edges of said length of cottonwool strip remaining open or exposed after combination with said length of cottonwool strip or rayon staple or combination of it are sealed to enclose the length of cottonwool strip or rayon staple or combination of it in fluffproof or fuzzproof form.

The tampon consists of a length of cottonwool strip or rayon staple or combination of it in a moisture-pervious, fluff-free or fuzz-free covering material that is of course impervious to any fluff in the constituent material of the cottonwool strip or rayon staple or combination of it plus recovery thread, which is compressed radially and/or axially in relation to the recovery thread, the solution provided by the invention is characterized in that the covering material consists at least partly of thermoplastic fibers and, at the edges which remain open or exposed after combination with the length of cottonwool strip or rayon staple or combination of it, is sealed to enclose the length of cottonwool strip or rayon staple or combination of it in "fluffproof" or fuzz-proof form. The open or exposed edges in question are, for example, cut or stamped edges. The covering material must contain fibers, for example thermoplastic fibers, which enable the material in question to be joined in this way, above all solely by the application of heat.

The invention also relates to a process for the production of a blank useful in the production of a tampon for feminine hygiene comprising the steps of (1) delivering individual lengths of strips of cottonwool or rayon staple or combination thereof onto a strip of covering material, at preselected intervals, (2) covering said individual lengths of cottonwool strip or rayon staple or combination of it with said covering material, said covering material in steps (1) and (2) being moisture-pervious fluff-free or fuzz-free covering material consisting at least partially of thermoplastic fibers, (3) sealing in fluffproof or fuzz-proof form the projecting surfaces of said covering material around the periphery of said individual lengths of cottonwool strip or rayon staple or combination of it (4) separating fluffproof covered and sealed individual lengths of cottonwool strip or rayon staple or combination of it, either before, during or after said sealing step, and (5) recovering a blank useful in the production of a tampon for feminine hygiene.

According to the invention, the edges which remain exposed after introduction of the cottonwool strip or rayon staple or combination of it into the covering material, followed by separation, particularly stamping, into individual sections are sealed to form the blank for the tampon. In the context of the invention, the expression "sealing" is understood to mean the joining of materials, for example by line or spot welding or bonding. Sealing may also be carried out first, followed by separation into individual sections.

Sections of a cottonwool strip or rayon staple or combination of it which are formed at a cutting or stamping station are placed at preselected intervals on a strip of a moisture-pervious fluff-free or fuzz-free covering material, after which the strip of covering material is folded over the length of cottonwool strip or rayon staple or combination of it, more particularly in overlapping fashion, from its longitudinal sides and, finally is first transversely separated and then sealed in the space between successive lengths of a strip of cottonwool or rayon staple or combination thereof or is first sealed and then separated or subjected to both operations at one and the same time.

Alternatively, it is also possible in accordance with the invention to use a sandwich process. In this case, lengths of a cottonwool strip or rayon staple or combination of it formed at a cutting station are again preferably placed at intervals from one another on a strip of the fluff-free or fuzz-free covering material, after which a second strip of the covering material is applied to the length of cottonwool strip or rayon staple or combination of it. Thereafter, the covering material which preferably projects beyond the length of cottonwool srip or rayon staple or combination of it on all sides in the sandwich thus formed is transversely separated in the space between successive lengths of cottonwool strip or rayon staple or combination of it, the layers of covering material being sealed together in fluffproof or fuzzproof form either beforehand or afterwards. As in the above-mentioned process, in which the longitudinal edges of the cottonwool strip or rayon staple or combination of it are protected by folding of the covering material around them, the steps of separation and sealing may also be carried out at one and the same time, depending on the tool used.

The all-round covering of tampons is obtained by using sealable nonwovens and similar fluffproof or fuzzproof covering materials. Soft, flexible materials with low weights per unit area (20 $g/m^2$ at most), which consist at least partly of thermoplastic fibers, are preferably used for this purpose. Basically, two methods may be used for production. In one of these two methods, the lengths of cottonwool strip are first wrapped from two sides in a strip of covering material at least twice as wide and then separated and sealed at the exposed edges or the last two steps are reversed, (stamping and sealing process). In the other process, the lengths of cottonwool strip are arranged—again at intervals from one another—between two separate strips of covering material, followed by stamping and sealing (or vice versa) in the space between two lengths of cottonwool strip or rayon staple or combination of it (sandwich stamping and sealing process).

More particularly, in the folding, stamping and sealing process shown in FIGS. 1 and 2, a strip 1 of cottonwool is first separated into the required lengths 4 at a cutting station 2, for example by means of a stamping gauge 3. The lengths 4 thus formed are then placed on a strip 5 of a nonwoven or similar covering material either in a line or after deflection through 90° from the delivery direction. The strip 5 of nonwoven may be delivered for example from below via a roller 6. The speed of travel of the strip 5 of nonwoven in the longitudinal direction 7 relative to the rate of advance of the strip 1 of cottonwool or rather to the rate of deposition of the lengths 4 of cottonwool strip is predetermined in such a way that just enough space a for forming two sealing seams or one sealing seam to be longitudinally cut through is left between two lengths 4 of cottonwool strip.

In the embodiment illustrated by way of example in FIG. 1, the width of the strip 5 of nonwoven is intended to be twice or more than twice the width of the cottonwool strip or rayon staple or combination of it 1 so that the strip 5 of nonwoven can be folded over and preferably overlaps the longitudinal edges 8 of the length 4 of cottonwool strip. If the longitudinal edges 9 of the strip 5 of nonwoven overlap, the particular length 4 of cottonwool strip or rayon staple or combination of it is sealed in particularly firmly against fluff in the overlap zone 10. The overlap zone 10 in FIG. 2 may also be used with advantage for attaching the recovery thread 11.

After the lengths 4 of cottonwool strip or rayon staple or combination of it following one another at the interval a on the strip 5 of nonwoven have been closed, the operations of stamping and sealing are carried out in the space a. The order in which they are carried out may be selected in the usual way, depending on the type of tools used. After the front and rear ends (in the longitudinal direction 7) of each enclosed length 4 of cottonwool strip have passed through the stamping and sealing station 12, the sealed-in section 13 formed is compressed in the usual way, for example as described in the foregoing, to form the finished tampon after attachment of the recovery thread 11 (FIG. 2). Depending on the compression process used, the sealed edges may be shifted onto the longitudinal surface or to the head and the end of the tampon.

In cases where it is desired to avoid hardening of the edges as a result of sealing, it is possible for example to apply spot sealing with less hardening in overall terms. A further improvement may be obtained by folding the sealed-in lengths of cottonwool strip or rayon staple or combination of it before or during compression in such a way that the sealed edges are situated inside the compressed tampon.

In the sandwich stamping and sealing process shown in FIG. 3, the lengths 23 of cottonwool strip or rayon staple or combination of it which are delivered from below at intervals a on a strip 22 of nonwoven via a roller 21, in the same way as shown in FIG. 1, are covered by a second strip 25 of nonwoven delivered from above via roller 24. The strips 22, 25 of nonwoven should be wider by at least twice the sealing seam than the lengths 23 of cottonwool strip. As the process continued, the steps of stamping and sealing are carried out in a stamping and sealing station 26 (sealing may again precede stamping), so that individual sections 27 of cottonwool strip or rayon staple or combination of it covered all-round in fluff-proof or fuzz-proof manner are obtained as shown in FIG. 4. In FIG. 4, the dotted lines represent the sealed margin of the individual sections 27. Further processing, including the attachment of a recovery thread, may be carried out in the usual way.

In the process illustrated in FIG. 3, stamping and/or sealing may also be carried out with a roller of the type shown in FIG. 5 which is provided on its surface with several adjacent patterns 28 for sealing and/or stamping and which is therefore suitable for simultaneously producing several adjacent lengths 29 of covered cottonwool strip or rayon staple or combination of it, as shown in FIG. 6.

The preceding specific embodiments are illustrative of the process of the invention. It is to be understood however, that other expedients known to those skilled in the art or disclosed herein, may be employed without departing from the spirit of the invention or the scope of the appended claims.

We claim:

1. A blank useful in the production of a tampon for feminine hygiene comprising a desired length of a strip of cottonwool or rayon staple or combination thereof encompassed in a moisture-pervious fluff-free or fuzz-free nonwoven covering material consisting at least partially of thermoplastic fibers where any edges of said length of a strip of cottonwool or rayon staple or combination thereof remaining open or exposed after combination of said nonwoven covering material with said length of a strip of cottonwool or rayon staple or combination thereof are sealed solely by the application of heat by line or spot welding or bonding to enclose the length of a strip of cottonwool or rayon staple or combination thereof in fluff-proof or fuzz-proof form.

2. The blank of claim 1 wherein said sealed edges are spot sealed.

3. The blank of claim 1 wherein all of the edges of said length of a strip of cottonwool or rayon staple or combination thereof remain open after combination with said covering material and are sealed solely by application of heat by line or spot welding or bonding all-around.

4. The blank of claim 1 wherein the opposite two edges of said length of a strip of cottonwool or rayon staple or combination thereof remain open after combination with said covering material and are sealed solely by application of heat by heat by line or spot welding or bonding.

5. A tampon for feminine hygiene comprising a cylindrically-compressed blank of claim 1 to which a recovery thread was attached.

6. The tampon of claim 5 wherein the sealing seams of said blank are partly enveloped or enclosed before said compression and are situated inside the finished tampon.

* * * * *